United States Patent
Bangsund et al.

(10) Patent No.: US 9,523,712 B2
(45) Date of Patent: Dec. 20, 2016

(54) EDDY CURRENT PROBE ROTATOR

(71) Applicant: The Boeing Company, Chicago, IL (US)

(72) Inventors: John Bangsund, Kent, WA (US); Jeffrey G. Thompson, Auburn, WA (US)

(73) Assignee: The Boeing Company, Chicago, IL (US)

( * ) Notice: Subject to any disclaimer, the term of this patent is extended or adjusted under 35 U.S.C. 154(b) by 488 days.

(21) Appl. No.: 14/166,729

(22) Filed: Jan. 28, 2014

(65) Prior Publication Data

US 2015/0212113 A1    Jul. 30, 2015

(51) Int. Cl.
*G01N 27/82* (2006.01)
*G01R 33/12* (2006.01)
*G01R 1/067* (2006.01)
*G01N 27/90* (2006.01)

(52) U.S. Cl.
CPC ......... *G01R 1/06705* (2013.01); *G01N 27/902* (2013.01)

(58) Field of Classification Search
CPC .............. G01R 31/2886; G01R 1/0408; G01R 31/2889; G01R 31/2601; G01R 1/06722; G01R 1/06733; G01R 31/3696; G01R 1/0433; G01R 1/067; G01R 1/203; G01R 27/28; G01R 31/021; G01R 31/024; G01R 31/045; G01R 31/06
USPC ............... 324/219, 220, 221, 237, 238, 222, 437,324/164, 137, 754.11–754.19, 755.01–758.01
See application file for complete search history.

(56) References Cited

U.S. PATENT DOCUMENTS

| | | | |
|---|---|---|---|
| 4,142,154 A * | 2/1979 | Couchman | G01N 27/9093 324/219 |
| 4,219,774 A | 8/1980 | Rogel et al. | |
| 4,379,261 A * | 4/1983 | Lakin | G01N 27/904 324/232 |
| 5,059,904 A | 10/1991 | Mazzone et al. | |

(Continued)

FOREIGN PATENT DOCUMENTS

| | | |
|---|---|---|
| EP | 2919002 A2 | 9/2015 |
| GB | 2273782 A | 6/1994 |

OTHER PUBLICATIONS

"European Application No. 14190970.5, Partial Search Report mailed Aug. 14, 2015", 6 pgs.

(Continued)

*Primary Examiner* — Jermele M Hollington
*Assistant Examiner* — Taqi Nasir
(74) *Attorney, Agent, or Firm* — Kwan & Olynick LLP

(57) ABSTRACT

Provided is an inspection apparatus that includes a rotation disk configured to spin about an axis of rotation. The rotation disk includes a probe bushing configured to securely hold a standard eddy current probe a predetermined distance above a surface to be examined by the probe. The rotation disk is further configured to adjustably hold the standard eddy current probe such that the radial offset of the probe from the axis of rotation is set using a radial positioning set screw that is coupled to the rotation disk via a first slotted arm. The predetermined distance is set using a probe height set screw configured to secure the probe within the probe bushing. An outer stationary housing is coupled to the rotation disk such that the rotation disk rotates within the outer stationary housing.

20 Claims, 12 Drawing Sheets

(56) References Cited

U.S. PATENT DOCUMENTS 7,352,176 B1 * 4/2008 Roach ............... G01N 27/9033
324/228

OTHER PUBLICATIONS

"ECS-3 Lightweight, Portable, Rotating Eddy Current Scanner", Uniwest , 2011, Retrieved from the Internet: <http://www.uniwest.com/ECS-3-Lightweight-Portable-Rotating-Eddy-Current-Scanner-P15.aspx>, Accessed on Jan. 28, 2014, 2 pgs.

Spencer, Floyd W. , "Inspection Reliability of a Nortec-30 Eddyscan System", Statistics and Human Factors Department, Sandia National Laboratories, Jan. 1994, 18 pgs.

* cited by examiner

EDDY CURRENT PROBE ROTATOR

BACKGROUND

In-service airplanes undergo regular inspections of various locations on the fuselage to detect various defects, such as cracks or imperfections. These inspections affect thousands of aircraft, with each aircraft undergoing inspection of tens of thousands of fastener locations. For instance, these locations can include fastener locations, doubler edges, and the like.

Eddy current inspections of fastener locations containing flush head fasteners account for a large percentage of the eddy current inspections performed on in-service airplanes. The current approach to eddy current inspections involves using a circle template to align an eddy current probe so that the probe can be translated around the perimeter of the fastener. Alignment of the probe with respect to the fastener is critical. If the probe passes over the interface between the fastener and the skin of the aircraft surface, a false crack signal will occur and the template must be repositioned to ensure that there is actually a crack and not just the false signal. This process is tedious, slow, and prone to mistakes. In addition, eddy current inspections are among the most time consuming inspection methods to perform and are not desirable for large inspection areas.

Current eddy probe inspections also involve various disadvantages. One disadvantage is that if the paint on the airplane is too thick, it must be stripped to permit alignment of the standard eddy current pencil or spot probes. Stripping the paint in this manner is costly and invasive since the paint will then need to be repaired after inspection. Another disadvantage is that eddy probe inspections are typically time intensive. For a typical fuselage, there can be more than 10,000 fasteners. Because the primary inspection method requires a ⅛ inch diameter probe to be manually raster scanned over the full perimeter of all the doubler edges on the fuselage of these airplanes, inspection of a single aircraft can take a significant amount of time. Yet another disadvantage is that typical inspection methods are limited to detecting surface cracks.

An alternative to manual probe inspections requires purchasing an entirely new system with a unique probe. In particular, a custom designed probe device can be produced for each size of fastener and probe. However, because there is a range of fastener sizes, numerous probe devices with special instruments would need to be produced, stored, and maintained in order to implement this alternative. Accordingly, these custom designed systems are costly, and not commonly used in the inspection of aircraft.

Current inspection methods continue to be tedious, time consuming, and prone to errors. In addition, conventional inspection apparatuses are typically limited to detecting surface cracks and may in some cases require the removal of paint from the airplane surface, thereby adding to costs and downtime. Consequently, there is a need for low cost, low skill inspection solutions that can be used to increase inspection reliability and also decrease inspector fatigue and inspection time.

SUMMARY

Provided are apparatus and methods for inspecting various locations on aircraft. One example of the present disclosure relates to an inspection apparatus. The inspection apparatus includes a rotation disk configured to spin about an axis of rotation. The rotation disk includes a probe bushing configured to securely hold a standard eddy current probe a predetermined distance above a surface to be examined by the probe. The rotation disk is further configured to adjustably hold the standard eddy current probe such that the radial offset of the probe from the axis of rotation is set using a radial positioning set screw that is coupled to the rotation disk via a first slotted arm. The predetermined distance is set using a probe height set screw configured to secure the probe within the probe bushing. An outer stationary housing is coupled to the rotation disk such that the rotation disk rotates within the outer stationary housing. A driving mechanism is configured to spin the rotation disk within the outer stationary housing such that the probe revolves about the axis of rotation. A second slotted arm is pivotally mounted with a first end to the outer stationary housing and slidably mounted with a second end to the probe bushing, thereby preventing the probe from rotating about a longitudinal axis of the probe when the probe rotates above the surface to be examined.

In one aspect, which may include at least a portion of the subject matter of any of the preceding and/or following examples and aspects, the surface to be examined includes an area surrounding a fastener, and the radial offset of the probe is adjusted according to the size of the fastener.

In one aspect, which may include at least a portion of the subject matter of any of the preceding and/or following examples and aspects, the surface to be examined includes doubler edges where there are no fasteners present, and the radial offset of the probe is adjusted to detect subsurface cracks at the doubler edges.

In one aspect, which may include at least a portion of the subject matter of any of the preceding and/or following examples and aspects, the fastener is a flush head fastener.

In one aspect, which may include at least a portion of the subject matter of any of the preceding and/or following examples and aspects, the outer stationary housing contacts the rotation disk via ball bearings disposed around a perimeter of the rotation disk.

In one aspect, which may include at least a portion of the subject matter of any of the preceding and/or following examples and aspects, the standard eddy current probe is a high frequency pencil probe.

In one aspect, which may include at least a portion of the subject matter of any of the preceding and/or following examples and aspects, the standard eddy current probe is a low frequency spot probe configured to detect subsurface defects.

In one aspect, which may include at least a portion of the subject matter of any of the preceding and/or following examples and aspects, the driving mechanism includes a rubber grommet that frictionally drives the rotation of the rotation disk, and wherein the driving mechanism includes a battery driven motor.

In one aspect, which may include at least a portion of the subject matter of any of the preceding and/or following examples and aspects, the outer stationary housing includes a bottom surface configured to contact an area around the surface to be inspected.

In one aspect, which may include at least a portion of the subject matter of any of the preceding and/or following examples and aspects, the outer stationary housing includes three points of contact configured to contact an area around the surface to be inspected.

In one aspect, which may include at least a portion of the subject matter of any of the preceding and/or following examples and aspects, the rotation disk is configured to stop spinning if the probe contacts any obstacle.

Another example of the present disclosure relates to a system including an inspection mechanism configured to adjustably hold an eddy current probe a predetermined distance above a surface to be inspected. The surface includes an area surrounding a fastener. The inspection mechanism includes a rotation disk configured to spin the eddy current probe about an axis of rotation above the surface to be inspected. The inspection mechanism includes an outer stationary housing within which the rotation disk is configured to spin. The system also includes an alignment tool configured to allow adjustment of the eddy current probe the predetermined distance above the surface and at a radial offset from the axis of rotation corresponding to the size of the fastener. The alignment tool includes an alignment pin against which the radial offset of the probe is configured to be set. The alignment tool includes a probe height adjustment pad upon which the predetermined distance of the probe is configured to be set.

In one aspect, which may include at least a portion of the subject matter of any of the preceding and/or following examples and aspects, the inspection mechanism further includes a slotted arm assembly that has a slotted arm with a first end pivotally mounted to the outer stationary housing and a second end slidably mounted to a probe bushing that securely holds the probe within the rotation disk. The slotted arm assembly prevents the probe from rotating about a longitudinal axis of the probe when the probe rotates above the surface.

In one aspect, which may include at least a portion of the subject matter of any of the preceding and/or following examples and aspects, the inspection mechanism is configured for placement inside an outer rim of the alignment tool to adjust the radial offset of the probe.

In one aspect, which may include at least a portion of the subject matter of any of the preceding and/or following examples and aspects, the inspection mechanism is configured for placement on top of an outer rim of the alignment tool to adjust the predetermined distance of the probe.

Another example of the present disclosure relates to a process. An inspection mechanism is positioned above a flush head fastener. The flush head fastener is secured to an aircraft surface. The inspection mechanism includes a standard eddy current probe configured to rotate a radial distance from a center of the fastener. A reading from the probe is received. The reading indicates an irregularity in the surface below the probe. The position of the inspection mechanism is adjusted until the reading indicates that there is no irregularity in the surface below the probe, thereby indicating that the probe is rotating about the center of the fastener. A defect in the aircraft surface is detected if the inspection mechanism cannot be positioned relative to the flush head fastener such that the reading does not detect an irregularity.

In one aspect, which may include at least a portion of the subject matter of any of the preceding and/or following examples and aspects, receiving a reading from the probe includes displaying an eddy current instrument signal.

In one aspect, which may include at least a portion of the subject matter of any of the preceding and/or following examples and aspects, the radial distance is determined by the size of the fastener.

In one aspect, which may include at least a portion of the subject matter of any of the preceding and/or following examples and aspects, the standard eddy current probe is a high frequency spot probe.

In one aspect, which may include at least a portion of the subject matter of any of the preceding and/or following examples and aspects, the standard eddy current probe is a low frequency spot probe configured to detect subsurface defects.

In one aspect, which may include at least a portion of the subject matter of any of the preceding and/or following examples and aspects, the probe rotates a fixed distance above the flush head fastener.

These and other embodiments are described further below with reference to the figures.

DETAILED DESCRIPTION OF EXAMPLE EMBODIMENTS

Figure 1A:
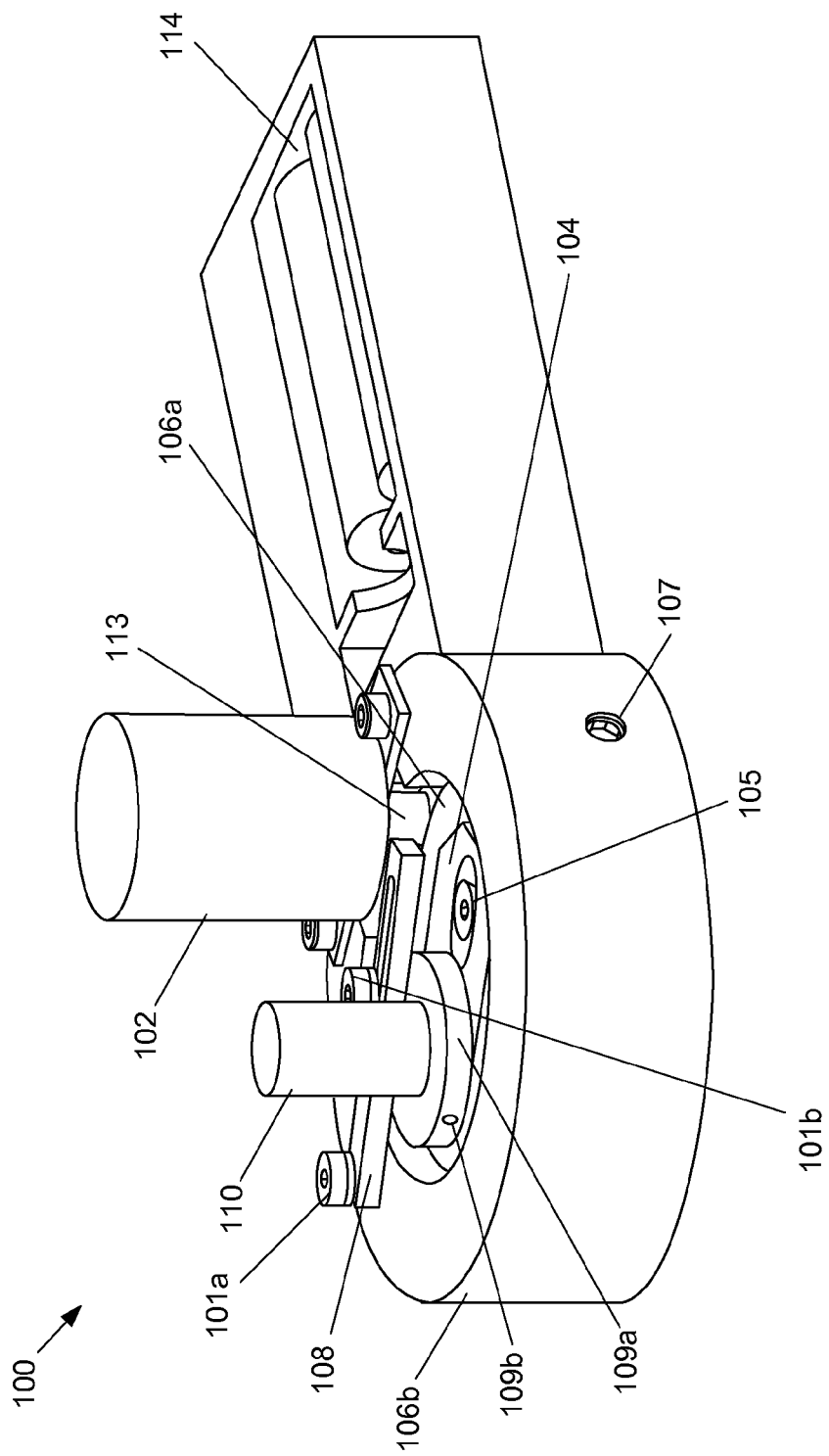
FIG. 1A is a diagrammatic representation of an inspection apparatus, in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Introduction

In-service airplanes require regular inspections of various locations of the aircraft to detect defects such as cracks or imperfections. For instance, these inspections can include inspections of fastener locations on areas such as the fuselage and other areas. In addition, current mandates require full fuselage inspections to detect doubler edge cracks on both the Boeing 737 and 757 models. These inspections affect thousands of aircraft, with each aircraft requiring inspection of tens of thousands of lineal inches of fuselage surface above bonded subsurface doubler locations.

Eddy current inspections of fastener locations containing flush head fasteners account for a large percentage of the eddy current inspections performed on in-service airplanes. The current approach to eddy current inspections involves using a circle template to align an eddy current probe so that the probe can be translated around the perimeter of the fastener. Current inspection methods continue to be tedious, time consuming, and prone to errors. In addition, conventional inspection apparatuses can be limited to detecting surface cracks and may in some cases require the removal of paint from the airplane surface, thereby adding to costs and downtime.

In some embodiments, an inspection apparatus and method that provide low cost, low skill inspection solutions that can be used to increase inspection reliability and also decrease inspector fatigue and inspection time. In particular, various examples of the inspection apparatus allow simplified eddy current inspection without the need for a circle template, or the more un-reliable free hand method, to guide an inspection probe and align it with a fastener edge. Furthermore, the inspection apparatus allows flush head fastener inspection to be performed rapidly with one hand. In addition, the inspection apparatus also supports eddy current surface inspection where it is necessary to pass the probe over suspect areas with a repetition of forward and backward motions. In some embodiments, the inspection apparatus can also be used as a wide area scanner to detect sub-surface cracks such as at fuselage doubler edges. Laboratory testing of the inspection apparatus described in particular embodiments shows that inspection time is reduced from 10 to 4 seconds per fastener, which provides a significant time and cost reduction to airline operators.

The apparatus and methods can be used during periodic airplane maintenance, and particularly in non-destructive testing (NDT) inspections according to various embodiments. Every airplane must undergo periodic maintenance in which NDT is a significant component. Many NDT procedures require inspections where various embodiments could be used. Furthermore, the apparatus and methods can be used by any airline operator, maintenance and repair depot, by personnel required to conduct non-destructive testing (NDT) inspections on structure, and the like, according to various embodiments.

Inspection Apparatus

With reference to FIG. 1A, shown is a diagrammatic representation of an inspection apparatus, in accordance with some embodiments. As shown, inspection apparatus 100 includes an inner rotation disk 106a positioned within an outer stationary housing 106b. As shown, outer stationary housing 106b can form a cylindrical shape with a flat bottom surface such that the inspection apparatus can contact and easily slide along a flat surface. In alternative embodiments, the outer stationary housing could be formed in other shapes with at least three physical points on the bottom that are configured to contact and slide along a flat surface to be inspected. For instance, an outer stationary housing could be formed with three points of contact to account for surface irregularities, such as a slight curvature of the part to be inspected, protruding, or cocked countersunk fastener heads, or the like.

In the present embodiment, probe bushing 109a, which can accommodate a standard probe 110, is coupled to inner rotation disk 106a by way of a slotted arm 104. The probe 110 can be secured in place within probe bushing 109a with a probe height set screw located at 109b. Set screw 109b can be oriented perpendicular to the axis of the probe 110 to achieve a snug fit. In some embodiments, probe bushing 109a is an adjustable probe holder that can accommodate a wide range of eddy current probe diameters. In these embodiments, inspection apparatus 100 can be used with various probes and instruments, thereby minimizing additional equipment costs and eliminating the need for costly custom designed inspection apparatus. According to various embodiments, one type of probe that can be used is a high frequency spot probe with a diameter of about ⅛ inch. The radial location of the probe with respect to the rotation axis of the rotation disk, also referred to as the radial offset, can be adjusted and secured by positioning screw 105, which is mounted to the rotation disk 106a via slotted arm 104. In the present embodiment, although positioning screw 105 can slide within slotted arm 104 when loosened, positioning screw 105 securely fastens slotted arm 104 to rotation disk 106a when tightened down. The radial offset of the probe can be adjusted to accommodate a wide range of fastener diameters and probe sizes.

In some embodiments, drive wheel 113 can spin rotation disk 106a within outer stationary housing 106b by providing frictional contact with the perimeter of rotation disk 106a. In particular embodiments, drive wheel 113 can be a rubber grommet that can provide friction driven rotation of rotation disk 106a. Drive wheel 113 can be powered by motor 102 and battery 114. In some embodiments, inspection apparatus 100 can be powered using 2 low-cost "C" batteries. In addition, in some embodiments, the inspection apparatus can operate at 2 rotational speeds to accommodate rotational speed sensitive inspection applications. According to various embodiments, the drive wheel 113 can spin rotation disk 106a in the range of about 200 to 500 rpm. Although the probe is designed to hover above a surface to be inspected, if the probe comes into contact with the surface or any other obstacle, the rotation disk 106a is configured to stop moving, according to various embodiments. In such embodiments, rotation disk 106a can stop moving when slippage between drive wheel 113 and rotation disk 106a occurs. Because the probe can stop rotating upon contact with another object, damage to the probe and any surface to be inspected can be avoided or minimized.

Figure 2A:
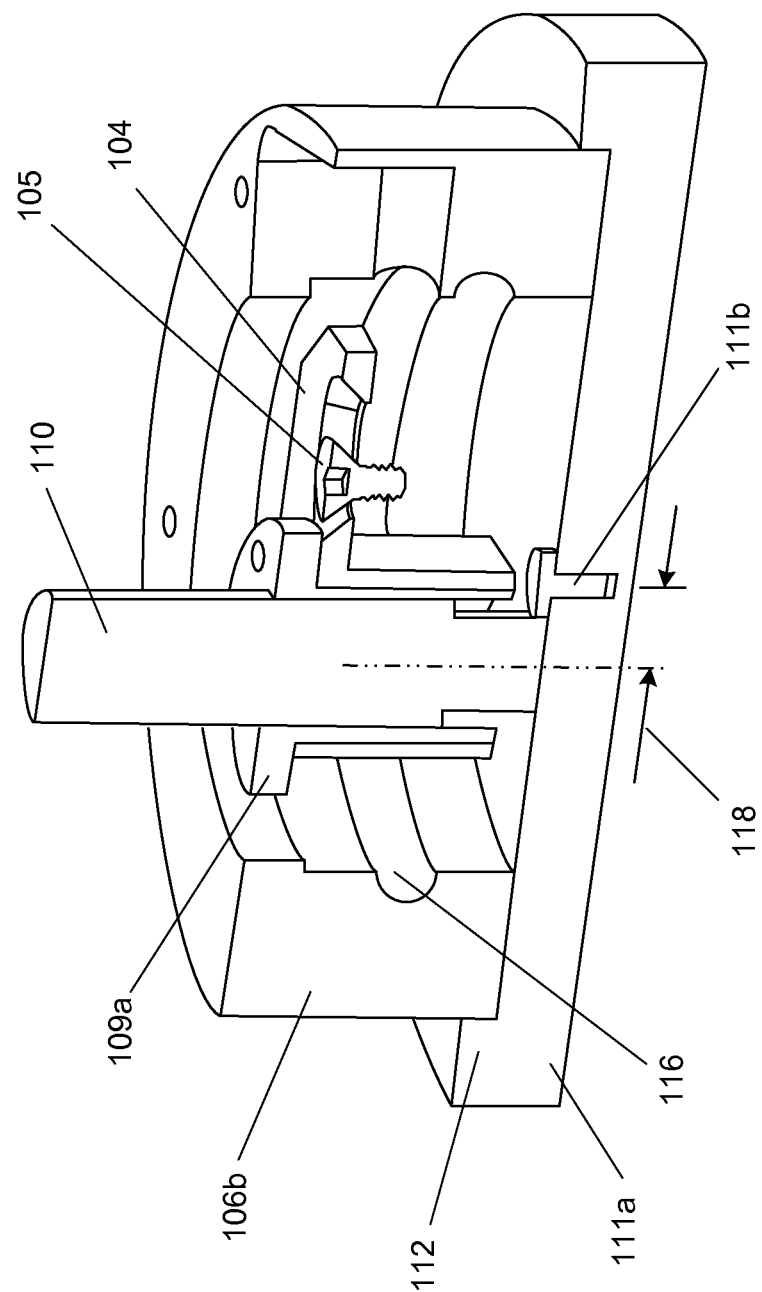
FIG. 2A is a diagrammatic representation of an inspection apparatus positioned over an alignment tool to achieve a desired radial offset, in accordance with some embodiments.
Figure 3A:
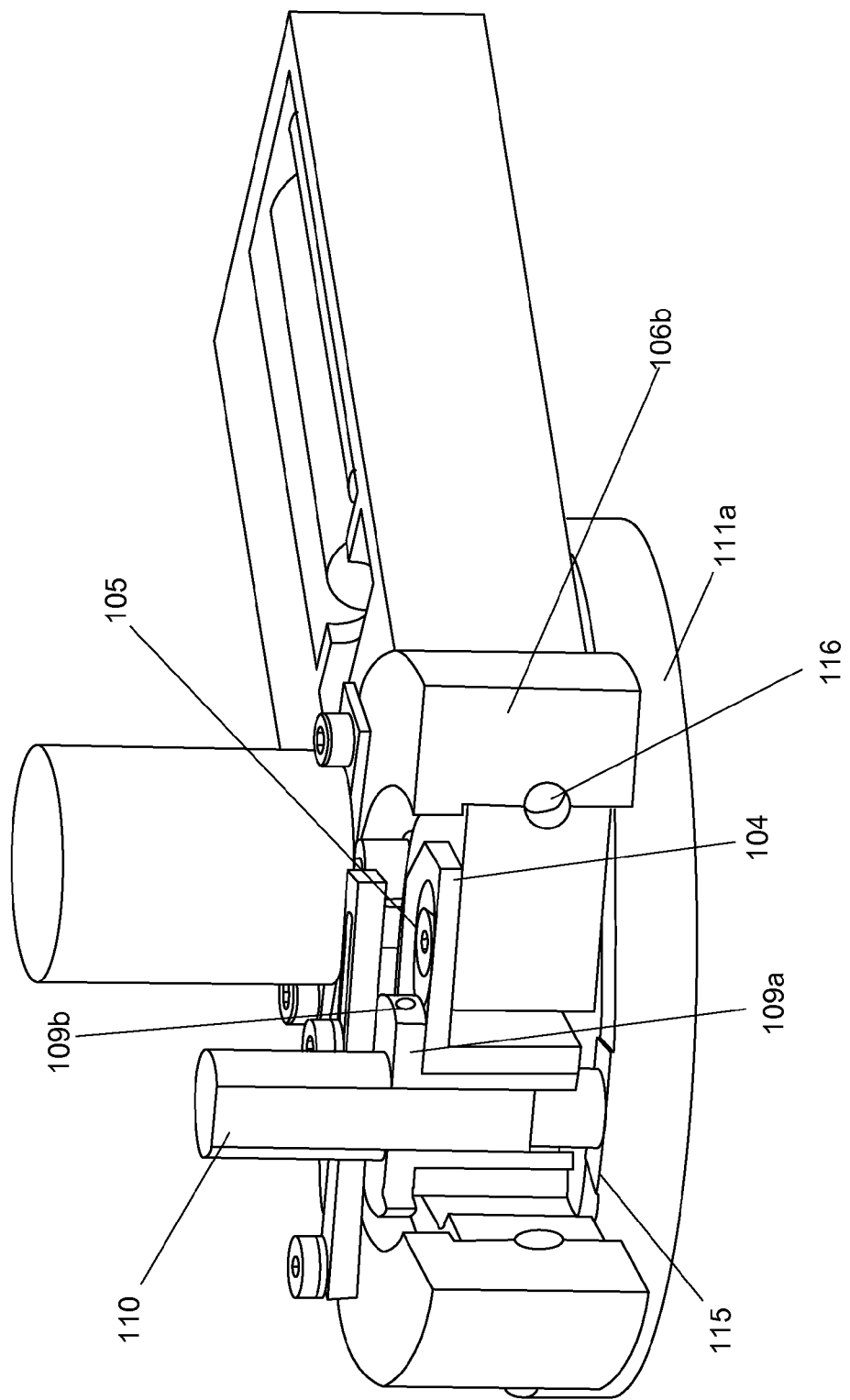
FIG. 3A is a diagrammatic representation of an inspection apparatus positioned over an alignment tool to achieve a desired probe height, in accordance with some embodiments.

In some embodiments, ball bearings can be located around the perimeter of rotation disk 106a such that contact between rotation disk 106a and stationary housing 106b is via the ball bearings. These ball bearings can be inserted through a portal 107 located within outer stationary housing 106b. This portal can feed the ball bearings into a channel 116 located between the outer stationary housing and the rotation disk, as shown in FIGS. 2A and 3A.

According to various embodiments, an orientation arm 108 is pivotally mounted to outer stationary housing 106b through pin 101*a* and slidably and pivotally mounted to probe bushing 109*a* through pin 101*b*. Pin 101*a* allows orientation arm 108 to pivot with respect to outer stationary housing 106*b* as probe bushing 109*a* rotates with rotation disk 106*a*. Pin 101*b* is configured to slide within a slot in orientation arm 108 and rotate within the slot, such that the probe bushing 109*a* remains in a constant orientation when rotation disk 106*a* is spinning. Specifically, orientation arm 108 is configured to keep probe bushing 109*a* and probe 110 from rotating about the longitudinal axis of the probe 110 such that any wires attached to probe 110 would not become tangled. Accordingly, as probe 110 rotates about a radial circumference defined by the location of probe 110 within rotation disk 106*a*, probe 110 stays at a constant orientation relative to its own axis, as described in more detail with regard to FIG. 1B.

Figure 1B:
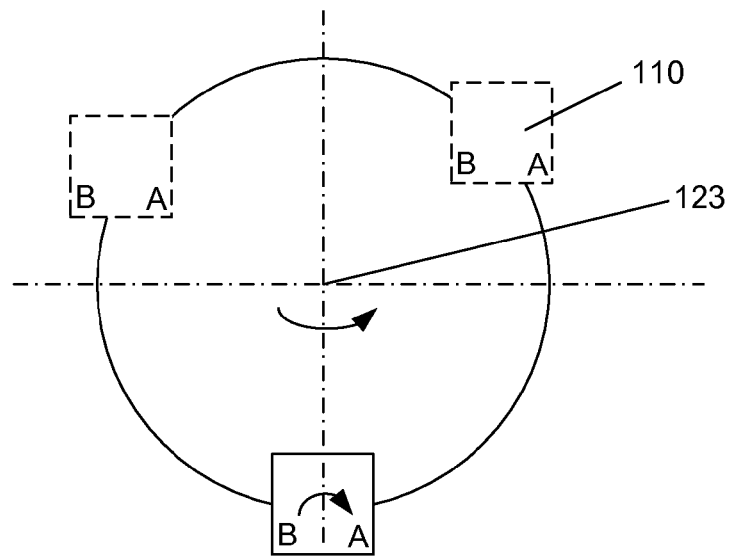
FIG. 1B is a diagrammatic representation of a probe rotating at a constant radial distance from a fastener center while maintaining a constant orientation relative to its own longitudinal axis, in accordance with some embodiments.

With reference to FIG. 1B, shown is a diagrammatic representation of a probe rotating at a constant radial distance from a fastener center while maintaining a constant orientation relative to its own longitudinal axis, in accordance with some embodiments. In particular, probe 110 rotates about fastener center 123 while maintaining a constant orientation relative to itself, such that "B" and "A" shown in the diagram remain in the same orientation around the perimeter of the rotation. By keeping the orientation of probe 110 constant, any cords or other attachments to probe 110 can remain plugged in without getting tangled even when probe 110 is rotating about fastener center 123 at high speeds.

Figure 1C:
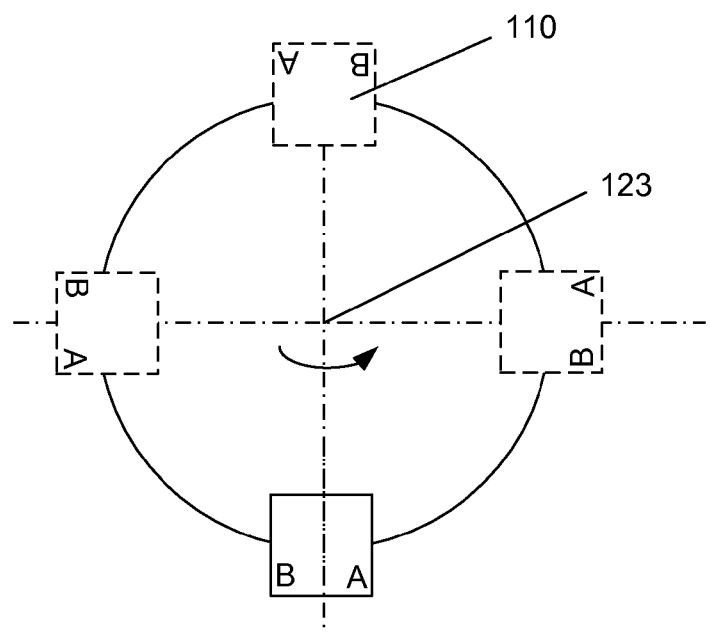
FIG. 1C is a diagrammatic representation of a probe rotating at a constant radial distance from a fastener center and rotating relative to its own longitudinal axis, in accordance with some embodiments.

Without the use of orientation arm 108, as shown in FIG. 1A, probe 110 would rotate about its own axis as it rotates about fastener center 123. With reference to FIG. 1C, shown is one example of a probe rotating at a constant radial distance from a fastener center 123 and rotating relative to its own longitudinal axis. In particular, as probe 110 rotates about fastener center 123, probe 110 maintains a constant orientation relative to the rotation disk (not shown) such that "B" and "A" as shown in the diagram appear to rotate about the axis of probe 110. This movement would tend to tangle any wires attached to probe 110 with each rotation. Although the present embodiment aims to reduce tangling by keeping probe 110 in a constant orientation with respect to itself by the use of orientation arm 108, there are embodiments in which rotation of the probe could be permitted. For instance, if the outer housing or sleeve of probe 110 can rotate while keeping the probe sensor and cords stationary relative to the probe axis, then the probe could be allowed to rotate. In another example, if the cords were attached to the probe via contacts that could slip within the probe housing, such that the probe would rotate but the cords would stay in a constant orientation, the probe could be allowed to rotate. However, according to various embodiments, it is preferable to keep the orientation of probe 110 stationary with regard to its own axis.

As described above with regard to various embodiments, inspection apparatus 100 is a compact device that allows an eddy current probe to be mechanically rotated around the perimeter of a fastener/skin interface to detect small cracks. According to various embodiments, the inspection apparatus 100 can be held and guided with a single hand during an inspection, rather than with two hands as required by the traditional circle template approach in which one hand is used to hold the circle template and the other is used to move the eddy current probe. Accordingly, use of the inspection apparatus 100 can eliminate the fatigue of the fingers that commonly occurs over time with the traditional circle template approach when a probe is manually manipulated using the fingers only while the other hand holds the circle template.

Alignment Tool Used to Calibrate Inspection Apparatus

According to various embodiments, inspection apparatus 100 can be adjusted to accommodate various sizes of fasteners and eddy current probes. In particular, the inspection apparatus can be adjusted such that a standard probe 110 can rotate around the perimeter of a flush head fastener to determine whether any cracks or irregularities are present in the surface (or skin) of the aircraft surrounding the fastener. More specifically, the probe can be positioned such that it passes around the perimeter of the fastener at a radial offset from the center of the fastener, and a predetermined distance above the surface of the aircraft to be inspected in order to obtain an eddy current reading that would indicate a crack or other irregularity.

With reference to FIG. 2A, shown is a diagrammatic representation of an inspection apparatus positioned over an alignment tool 111*a* to achieve a desired radial offset of probe 110, in accordance with some embodiments. It should be noted that some components of the inspection apparatus are not shown in this view in order to not obscure the diagram and description. For instance, rotation disk 106*a* is not shown in order to better illustrate the alignment of the apparatus.

In the present embodiment, alignment pin 111*b* is positioned at the center of alignment tool 111*a* and is selected to position probe 110 with a radial offset 118. According to various embodiments, radial offset 118 corresponds to a flush head fastener with a radius nearly equal to the radial offset 118. More specifically, radial offset 118 corresponds to the location just outside the perimeter of the flush head fastener such that probe 110 passes over the surface of the aircraft surrounding the flush head fastener, according to various embodiments.

Furthermore, in some embodiments, outer stationary housing 106*b* is positioned within alignment tool 111*a*, such that the outer perimeter of outer stationary housing 106*b* fits within a circumferential ridge of alignment tool 111*a*. Probe 110 is located within probe bushing 109*a*, and radial positioning set screw 105 can be loosened to allow bushing 109*a* and probe 110 to move radially along the rotation disk via slotted arm 104. The desired probe radial offset is established by sliding the probe 110 until it makes contact with the alignment pin 111*b*. More specifically, probe 110 can be adjusted to abut against the edge of alignment pin 111*b*. Once probe 110 is positioned, radial positioning set screw 105 can be tightened to secure probe bushing 109*a* at this radial distance.

Figure 2B:
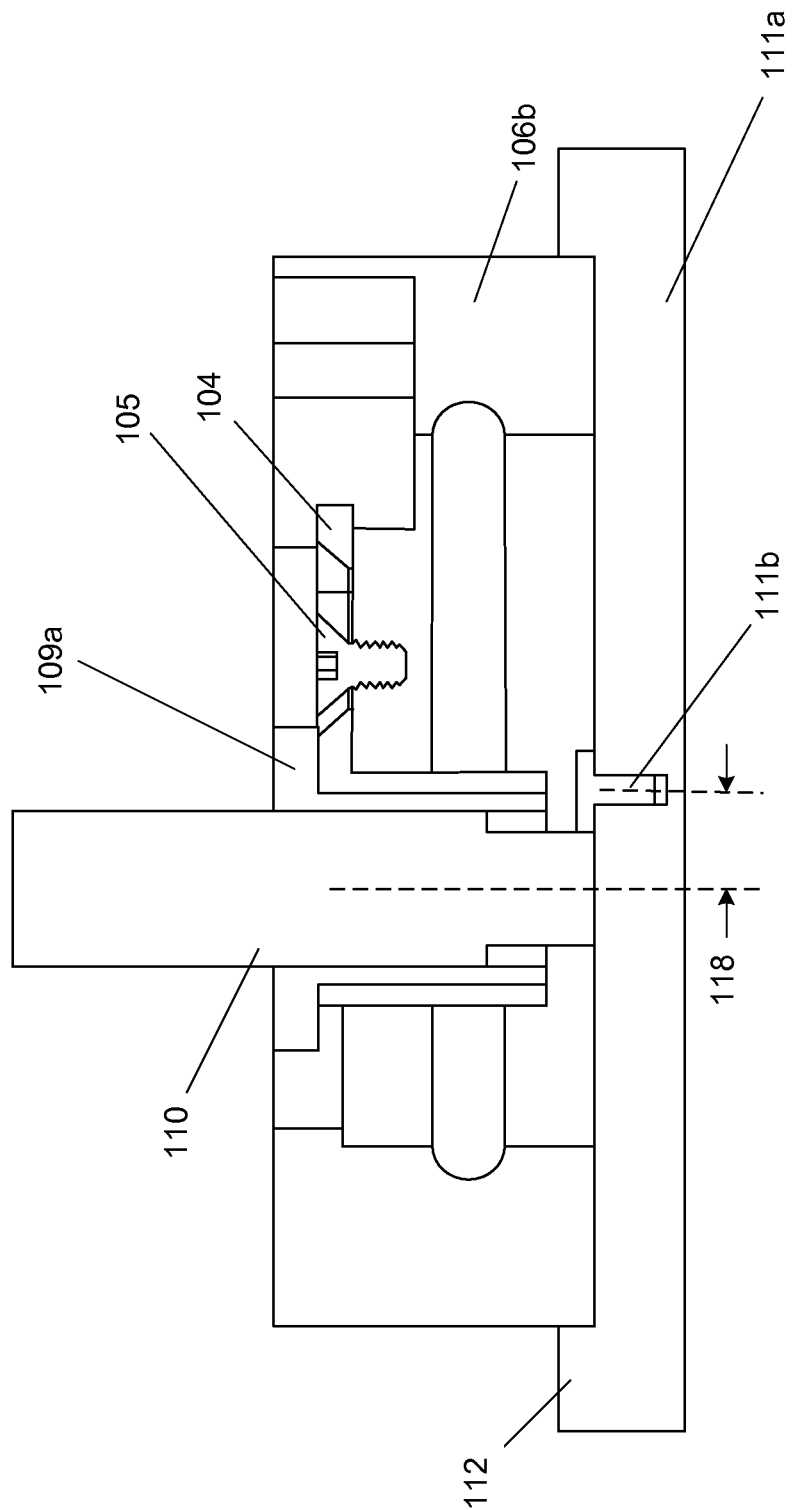
FIG. 2B is another diagrammatic representation of an inspection apparatus positioned over an alignment tool to achieve a desired radial offset, in accordance with some embodiments.

FIG. 2B shows another diagrammatic representation of the inspection apparatus positioned over the alignment tool shown in FIG. 2A, but in a cross-sectional view. As shown, outer stationary housing 106*b* is positioned within alignment tool 111*a* and probe 110 is positioned within probe bushing 109*a* and abutted against alignment pin 111*b*. Radial positioning set screw 105 is secured within slotted arm 104 to secure this radial alignment of probe 110.

As shown in FIGS. 2A and 2B, inspection apparatus 100 can be adjusted for the inspection of a wide range of flush head fasteners of different sizes. In particular, alignment pins 111*b* of different sizes can be used depending on the particular fastener size to be inspected and the probe diameter used. By allowing adjustment of the inspection apparatus 100, this single device can be used to inspect a large range of fastener diameters quickly and accurately. Furthermore, using an alignment tool to calibrate or adjust the settings of inspection apparatus allows repeatability of the settings and provides consistency and efficiency for inspections.

Figure 3B:
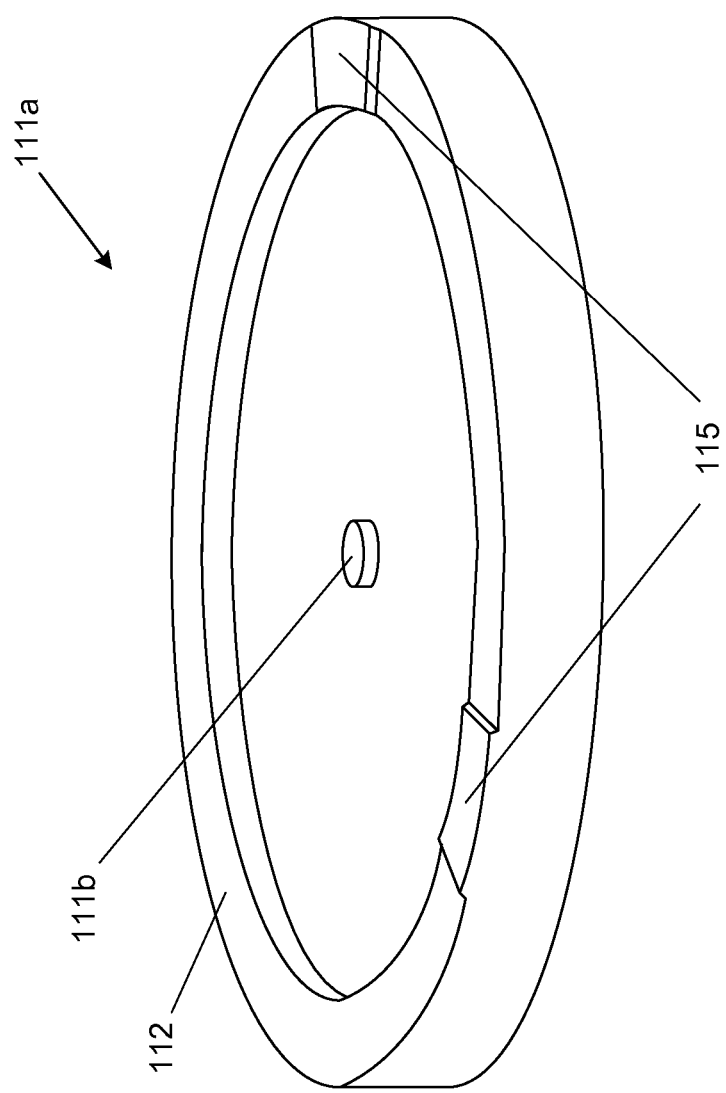
FIG. 3B is a diagrammatic representation of an alignment tool, in accordance with some embodiments.

As described above with regard to FIGS. 2A and 2B, alignment tool 111a can be used to position probe 110 radially. In addition, alignment tool 111a can be used to position the height of probe 110 a predetermined distance above the surface of the material to be tested without coming into contact with the material itself. FIGS. 3A and 3B illustrate how alignment tool 111a can be used to position the height of probe 110 this predetermined distance.

With reference to FIG. 3A, an inspection apparatus positioned over an alignment tool to achieve a desired probe height is illustrated. In particular, inspection apparatus 100 is placed on top of alignment tool 111a such that outer stationary housing 106b rests on the outer rim 112 (shown in FIGS. 2A, 2B and 3B) of alignment tool 111a and the probe rests on top of probe height adjustment pad 115. Typical heights of probe height adjustment pad 115 are 0.005", 0.010", and 0.015," although various heights can be used depending on the particular application. Once probe 110 is resting on probe height adjustment pad 115, probe height set screw 109b can be tightened against probe 110 to secure the probe in place. Probe height set screw 109b is oriented perpendicular to the axis of probe 110 and passes through probe bushing 109a. According to various embodiments, because probe height set screw 109b can be tightened to create a snug fit for a variety of probe sizes, a wide range of eddy current probe diameters can be used with the inspection apparatus. In some embodiments, various bushings with unique inner diameters can be used to accommodate various probes.

Once the inspection apparatus is removed from the alignment tool 111a, the bottom of probe 110 will be positioned such that when the inspection apparatus is placed on a surface to be inspected, probe 110 hovers above the surface a predetermined distance without touching it. Raising the probe 110 above the surface allows non-invasive inspections of aircraft surfaces, thereby preventing scratches to the inspection surfaces and avoiding damage and wear to the probe head.

Figure 4A:
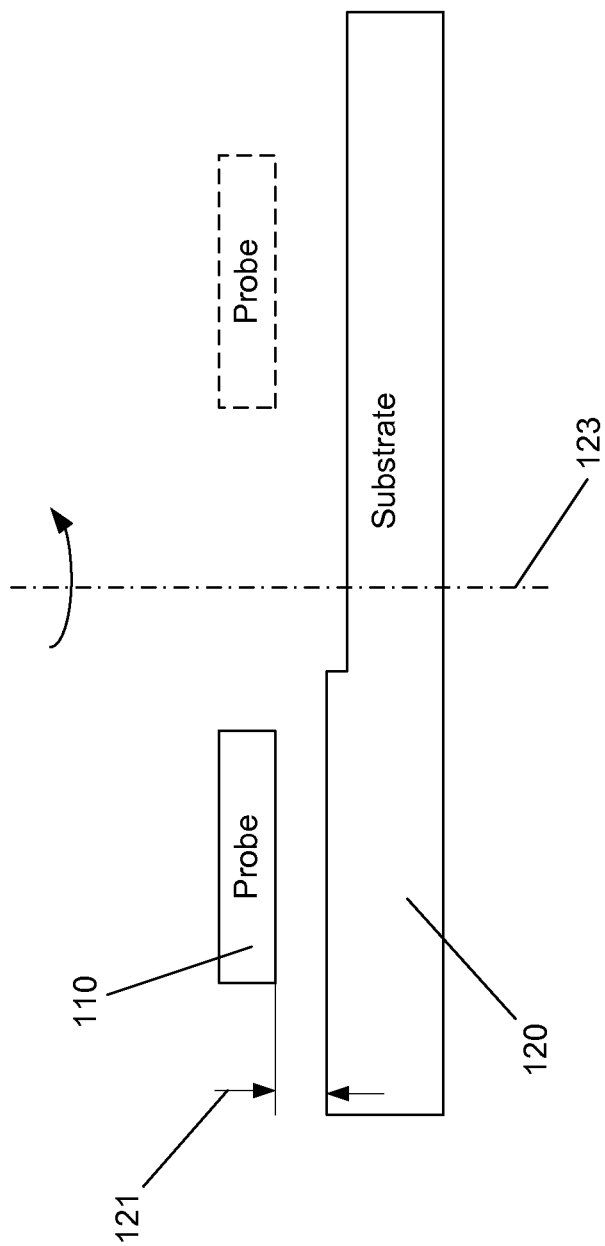
FIG. 4A is a diagrammatic representation of a probe passing over an aircraft surface, in accordance with some embodiments.

According to various embodiments, adequate space between the probe 110 and an inspection surface is critical to providing non-invasive testing of aircraft surfaces. As shown in FIG. 4A, probe 110 rotates about fastener center 123 during an inspection of an aircraft surface 120. In some instances, aircraft surface 120 may be uneven, as shown, due to surface irregularities, joints between surfaces, raised rivet heads, or other features. In order to avoid damage to aircraft surface 120 and to probe 110, a predetermined distance 121 must be maintained between the aircraft surface 120 and probe 110. By properly setting the probe height, as described in connection with FIG. 3A, this predetermined distance 121 can be maintained. It is also important that the probe 110 be located close enough to the surface of the surface 120 to be inspected because the eddy current signal strength will decay as the separation between probe 110 and aircraft surface 120 is increased.

As described above, alignment tool 111a can be used to adjust the radial probe offset and the desired probe height for an inspection apparatus 100. With reference to FIG. 3B, an alignment tool 111a is illustrated. As shown, alignment tool 111a includes an outer rim 112 within which the outer stationary housing 106b can be positioned, as described above with regard to FIGS. 2A and 2B. Alignment tool 111a also includes probe height adjustment pads 115, which can be used to adjust the height of probe 110, as described above with regard to FIG. 3A. In addition, alignment pin 111b can be used to adjust the radial offset of probe 110 as described with regard to FIGS. 2A and 2B. As mentioned above, different alignment pins 111b can be used with different sizes depending on the radial offset desired for probe 110.

Figure 4B:
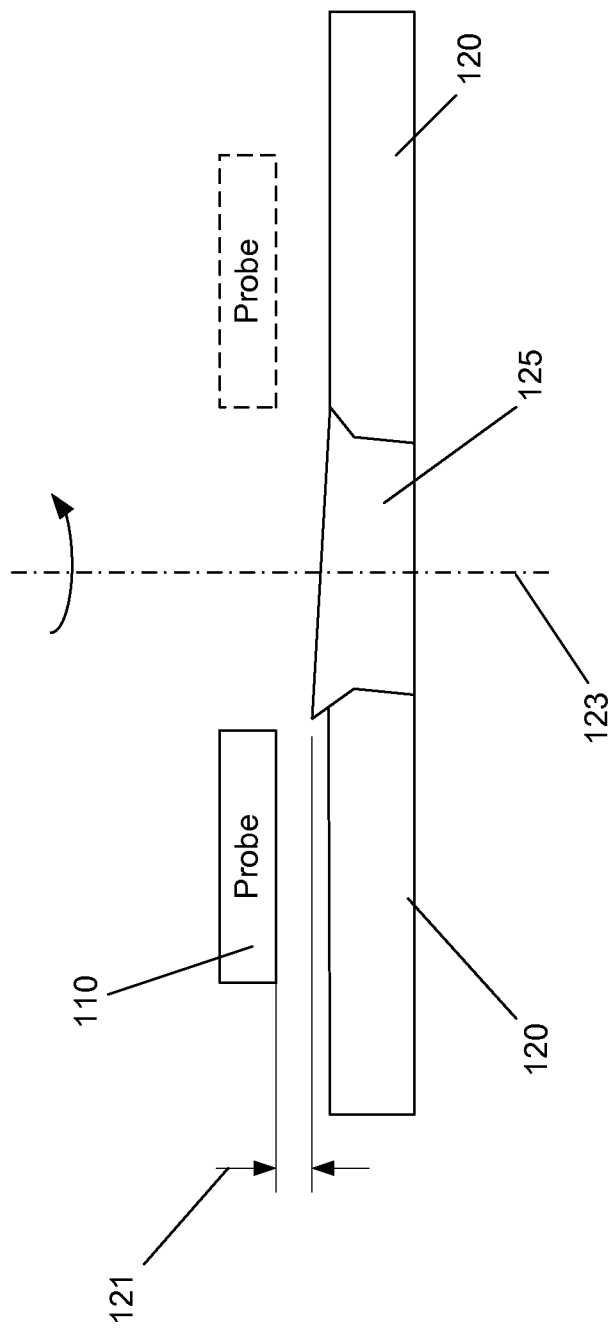
FIG. 4B is another diagrammatic representation of a probe passing over an aircraft surface, in accordance with some embodiments.

With reference to FIG. 4B, shown is another example of a probe rotating above a fastener center during an inspection. More specifically, probe 110 rotates about fastener center 123 during an inspection of an aircraft surface 120. In this embodiment, a typical cocked fastener 125 is shown protruding above aircraft surface 120. In order to avoid damage to aircraft surface 120 and to probe 110, a predetermined distance 121 must be maintained between the aircraft surface 120 and probe 110. By properly setting the probe height, as described in connection with FIG. 3A, this predetermined distance 121 can be maintained. It is also important that the probe 110 be located close enough to the surface of the surface 120 to be inspected because the eddy current signal strength will decay as the separation between probe 110 and aircraft surface 120 is increased.

Figure 4C:
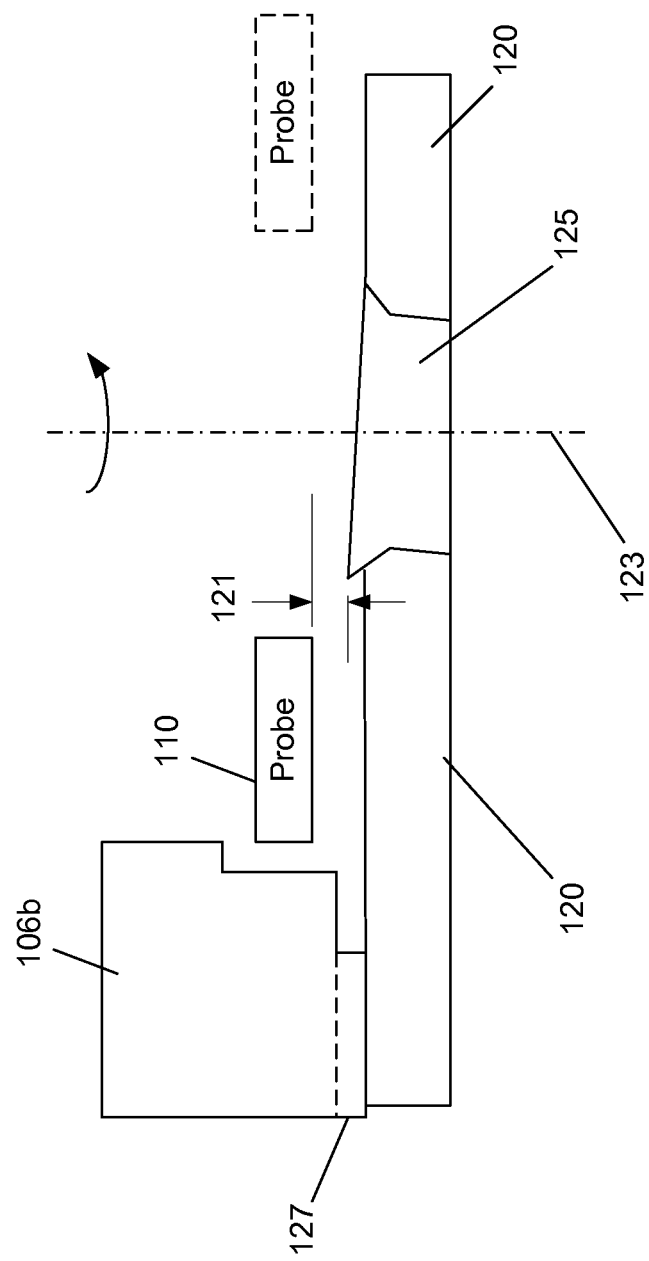
FIG. 4C is another diagrammatic representation of a probe passing over an aircraft surface, in accordance with some embodiments.

As described above with regard to FIG. 1A, stationary housing 106b can include three contact points that contact aircraft surface 120. With reference to FIG. 4C, shown is a probe rotating above a fastener center during an inspection and a cross-sectional view of one of the three contact points, according to a particular embodiment. More specifically, probe 110 rotates about fastener center 123 during an inspection of an aircraft surface 120. In this embodiment, a typical cocked fastener 125 is shown protruding above aircraft surface 120. In order to avoid damage to aircraft surface 120 and to probe 110, a predetermined distance 121 must be maintained between the aircraft surface 120 and probe 110. In the present embodiment, a cross-sectional view of stationary housing 106b is shown with contact point 127. In some examples, contact point can include a thickness of 0.020 feet and this contact point can be located in three places along the perimeter of the base of stationary housing 106b.

Alignment of Probe Using Eddy Current Instrument Signal

Figure 5A:
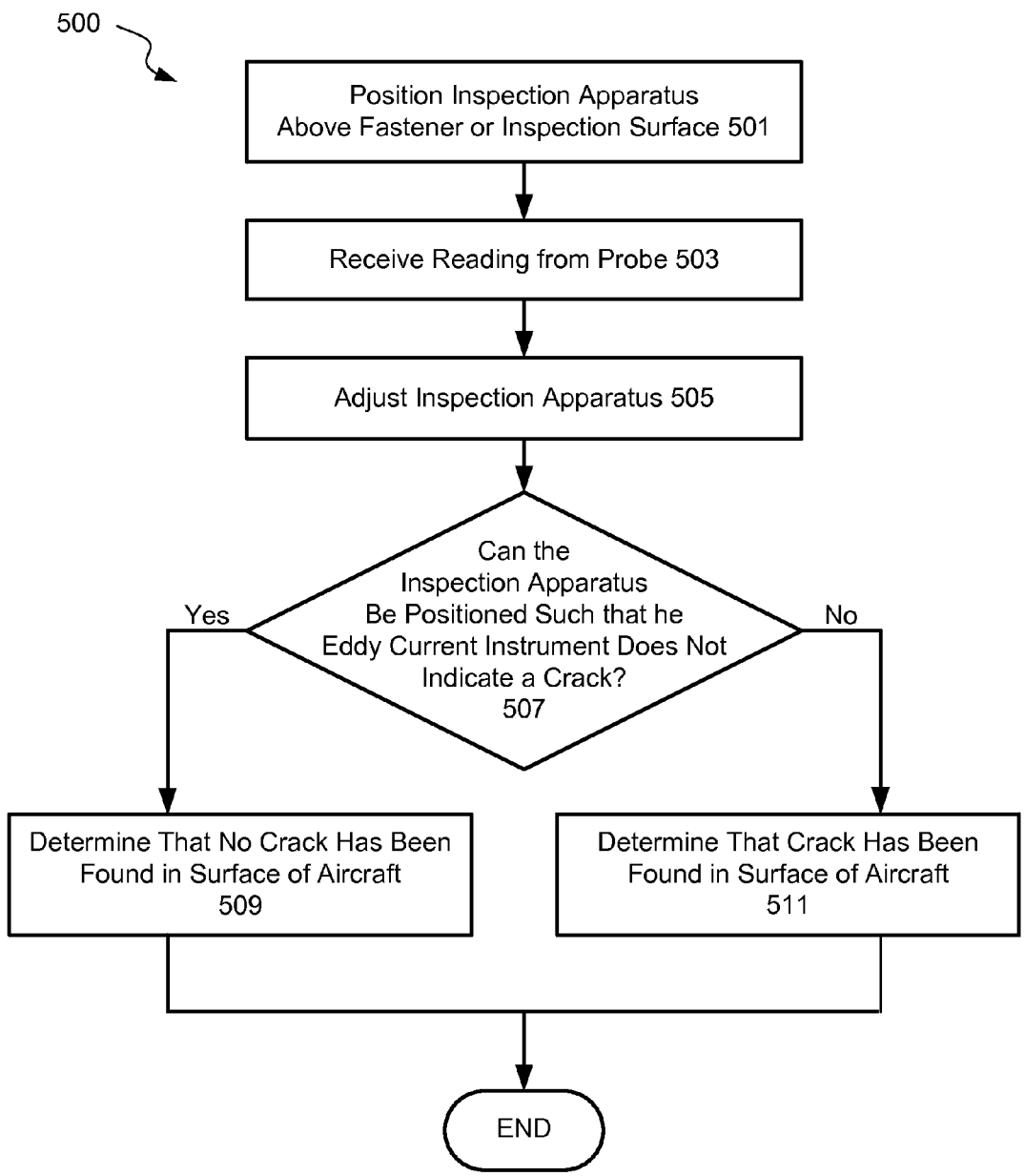
FIG. 5A is a flow process diagram illustrating an inspection process, in accordance with some embodiments.

According to various embodiments, the inspection apparatus eases manual alignment difficulties that occur with the circle template approach. In particular, the inspection apparatus can be positioned using an observed eddy current instrument signal obtained while the probe spins above a fastener and/or surface to be inspected. With reference to FIG. 5A, shown is a flow process diagram illustrating an inspection process, in which the probe can be positioned relative to a fastener or inspection surface and a determination can be made about whether a crack or other irregularity is present in the aircraft surface surrounding the fastener or within the inspection surface.

In some embodiments, the inspection apparatus is positioned above a fastener or inspection surface at 501. Because the eddy current probe is held above the surface a predetermined amount, there is no wear on the eddy current probe and there is no risk of damaging the paint on the surface of the area to be inspected when the probe is rotating. In addition, because the probe is kept slightly above the surface, the effects of surface roughness, imperfections in surface geometry, and cocked flush head fasteners do not interfere with the inspection process.

Figure 5B:
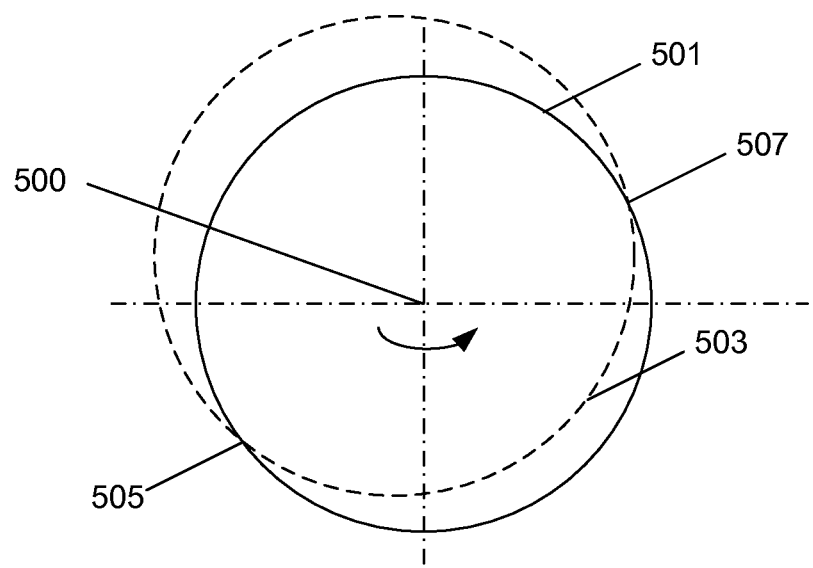
FIG. 5B is a diagrammatic representation of the path of a probe relative to a fastener head, in accordance with some embodiments.

Once the inspection apparatus is positioned above a fastener or inspection surface, a reading can be received from the probe at 503 and an eddy current instrument signal can be observed. As shown in FIG. 5B, when the center of the eddy current probe rotator (inspection apparatus) is not positioned directly over the center of a fastener, the probe will pass over two locations where there is a fastener/skin interface (where the skin is the surface of the aircraft), and these locations will register a signal on the eddy current instrument as a crack. In particular, the fastener/skin boundary 501 is shown along with the fastener center 500. The path of the probe 503 is indicated by dotted lines. When the path of the probe 503 is not aligned with the fastener, as shown in this figure, the path of the probe 503 will overlap the fastener/skin boundary 501 at two positions 505 and 507.

With reference again to FIG. 5A, the position of the inspection apparatus can be adjusted based on the readings received from the probe positions 505 and 507. More specifically, the inspection apparatus can be indexed or moved a small amount relative to two orthogonal axes as the eddy current instrument display is monitored. When the inspection apparatus is positioned directly over the center of the fastener, no crack signal will register on the eddy current instrument display because the probe is uniformly passing over the surface of the aircraft to be inspected or the seam between the fastener and the skin of the surface to be inspected. Accordingly, centering the probe over the fastener head is achieved when the eddy current instrument display indicates that there is no crack.

Figure 5C:
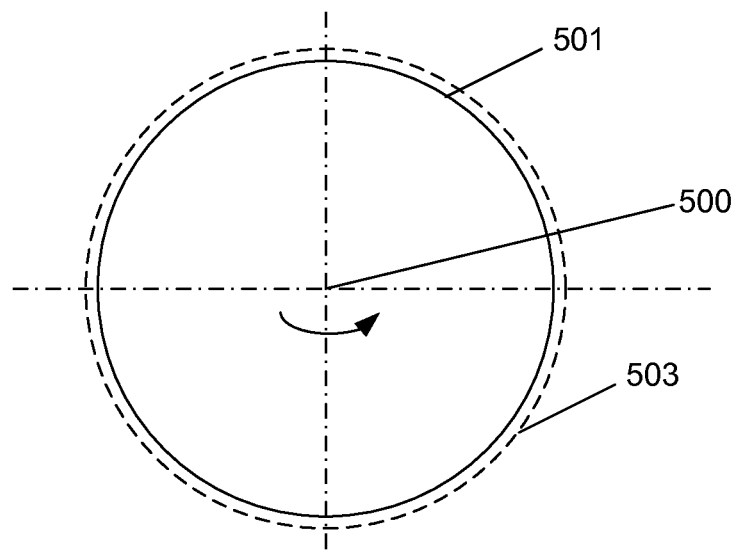
FIG. 5C is another diagrammatic representation of the path of a probe relative to a fastener head, in accordance with some embodiments.

As shown in FIG. 5C, when the path of the probe 503 is centered relative to the fastener center 500, the probe passes around the perimeter of fastener/skin interface 501 and does not register a crack based on the positioning of the inspection apparatus. Because the inspection apparatus rigidly holds the eddy current probe above the surface to be inspected at a particular radial distance, the probe can be scanned over a short edge margin and even overhang the fastener/skin interface around the perimeter of the fastener without registering a crack signal. FIG. 5C shows a small distance between the fastener/skin boundary 501 and the path of the probe 503, indicating that only the surface/skin of the aircraft near the fastener will be scanned. As described above, if the path of the probe 503 were to have a slightly smaller radius such that the probe overlapped the fastener/skin interface, the reading from the probe would detect a consistent crack all the way around the scan since the interface would be consistently registered throughout the probe rotation, thus there would be no "noise" or crack signal that spikes on the eddy current instrument display. In addition, because the inspection apparatus holds the probe perpendicular to the surface, unwanted noise signals that decrease the signal to noise ratio are eliminated that would typically occur during manual scans if the probe is slightly angled from perpendicular.

In the present embodiment, with reference again to FIG. 5A, a determination is then be made about whether the inspection apparatus can be positioned such that the eddy current instrument does not return a signal indicating a crack or other irregularity at 507. Typically, the minimum detectable crack is in the range of about 1/10 inch. The presence of a crack will not allow the probe to be centered without registering a signal from the crack. Since a mis-aligned probe produces a crack signal, a fastener hole will be rejected as cracked unless the inspector can minimize the signal appropriately by properly centering the probe. The ability to achieve a minimized signal provides for a positive indication that the inspection is done correctly. This provides a distinctive advantage over traditional methods because no such inspector feedback is available using the conventional eddy current methods.

If the inspection apparatus can be positioned relative to the fastener such that the eddy current instrument signal can be minimized, then a determination can be made at 509 that no crack has been found at this location. However, if the inspection apparatus cannot be positioned to minimize the eddy current instrument signal, then at 511 a determination can be made that a crack has indeed been found at this location.

According to various embodiments, the inspection method described can be performed through thick paint, since the inspector uses the general knowledge of the fastener position and spacing and the signal on the eddy current instrument to align the probe, rather than a visual probe alignment. Furthermore, this method can be used to detect subsurface cracks, according to some embodiments. Specifically, the inspection apparatus can be employed to automatically scan the probe over the edge of a subsurface doubler to detect cracks. In various examples, scanning the probe over a subsurface doubler may include scanning over an aircraft surface without any fasteners. Additionally, because the diameter over which the probe moves is in the range of about 2 inches, the precision by which the probe must be placed to ensure adequate inspection of a doubler edge (hidden from the airplane exterior) to detect a subsurface crack is reduced. Furthermore, as the inspection apparatus is translated along the perimeter of the doubler edge, two inspection opportunities will be provided because the tool will cause the rotating eddy current probe to pass over a crack site twice. Accordingly, the area swept out by the rotating eddy current probe is fully inspected twice as the tool is moved over the inspection area. In some examples, the inspection apparatus can be used with a low frequency spot probe that can detect subsurface cracks. In some embodiments, an eddy current sliding probe or eddy current array probe can be replaced by the eddy current rotator.

Examples of Aircraft

Figure 6A:
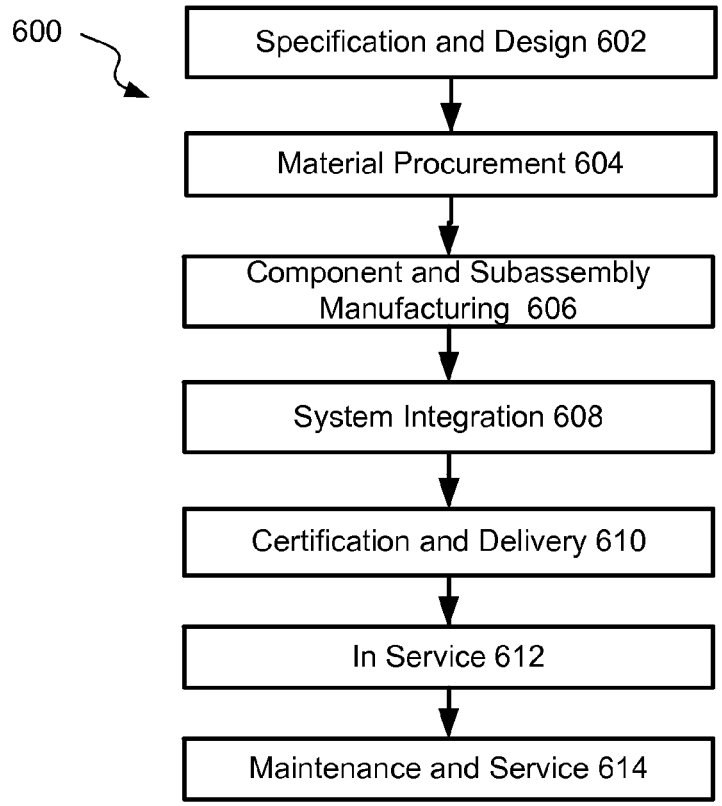
FIG. 6A is a process flowchart reflecting key operations in the life cycle of an aircraft from early stages of manufacturing and to entering service, in accordance with some embodiments.

An aircraft manufacturing and service method 600 shown in FIG. 6A and an aircraft 630 shown in FIG. 6B will now be described to better illustrate various features of processes and systems presented herein. During pre-production, aircraft manufacturing and service method 600 may include specification and design 602 of aircraft 630 and material procurement 604. The production phase involves component and subassembly manufacturing 606 and system integration 608 of aircraft 630. Thereafter, aircraft 630 may go through certification and delivery 610 in order to be placed in service 612. While in service by a customer, aircraft 630 is scheduled for routine maintenance and service 614 (which may also include modification, reconfiguration, refurbishment, and so on). While the embodiments described herein relate generally to servicing of commercial aircraft, they may be practiced at other stages of the aircraft manufacturing and service method 600.

Each of the processes of aircraft manufacturing and service method 600 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

Figure 6B:
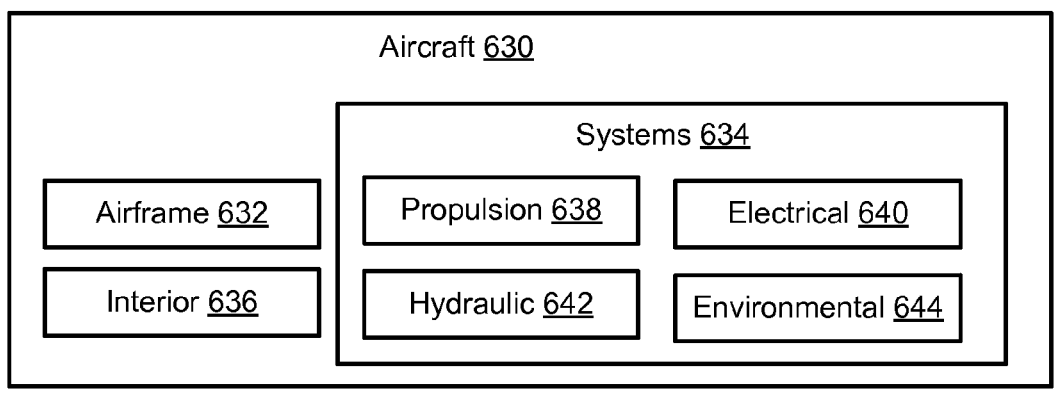
FIG. 6B is a block diagram illustrating various key components of an aircraft, in accordance with some embodiments.

As shown in FIG. 6B, aircraft 630 produced by aircraft manufacturing and service method 600 may include airframe 632, interior 636, and multiple systems 634. Examples of systems 634 include one or more of propulsion system 638, electrical system 640, hydraulic system 642, and environmental system 644. Any number of other systems may be included in this example. Although an aircraft example is shown, the principles of the disclosure may be applied to other industries, such as the automotive industry.

Apparatus and methods embodied herein may be employed during any one or more of the stages of aircraft manufacturing and service method 600. For example, without limitation, components or subassemblies corresponding to component and subassembly manufacturing 606 may be fabricated or manufactured in a manner similar to components or subassemblies produced while aircraft 630 is in service.

Also, one or more apparatus embodiments, method embodiments, or a combination thereof may be utilized during component and subassembly manufacturing 606 and system integration 608, for example, without limitation, by substantially expediting assembly of or reducing the cost of aircraft 630. Similarly, one or more of apparatus embodiments, method embodiments, or a combination thereof may be utilized while aircraft 630 is in service, for example, without limitation, to maintenance and service 614 may be used during system integration 608 and/or maintenance and service 614 to determine whether parts may be connected and/or mated to each other.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. An inspection apparatus comprising:
a rotation disk configured to spin about an axis of rotation,
wherein the rotation disk comprises a probe bushing configured to securely hold an eddy current probe a predetermined distance above a surface to be examined by the eddy current probe,
wherein the rotation disk is configured to adjustably hold the eddy current probe such that a radial offset of the eddy current probe from the axis of rotation is set using a radial positioning set screw coupled to the rotation disk using a first slotted arm and the predetermined distance is set using a probe height set screw configured to secure the eddy current probe within the probe bushing;
an outer stationary housing coupled to the rotation disk such that the rotation disk rotates within the outer stationary housing;
a driving mechanism configured to spin the rotation disk within the outer stationary housing such that the eddy current probe revolves about the axis of rotation; and
a second slotted arm comprising a first end pivotally mounted to the outer stationary housing and a second end slidably mounted to the probe bushing thereby preventing the eddy current probe from rotating about a longitudinal axis of the eddy current probe when the eddy current probe rotates above the surface to be examined.

2. The inspection apparatus of claim 1, wherein the radial offset of the eddy current probe is adjusted according to a size of a fastener on the surface to be examined and a size of the eddy current probe.

3. The inspection apparatus of claim 2, wherein the fastener is a flush head fastener.

4. The inspection apparatus of claim 1, wherein the surface to be examined includes a doubler edge where there are no fasteners present, and the radial offset of the eddy current probe is adjusted to detect subsurface cracks at the doubler edge.

5. The inspection apparatus of claim 1 wherein the outer stationary housing contacts the rotation disk via ball bearings disposed around a perimeter of the rotation disk.

6. The inspection apparatus of claim 1, wherein the eddy current probe is a high frequency spot probe.

7. The inspection apparatus of claim 1, wherein the eddy current probe is a low frequency spot probe configured to detect subsurface defects.

8. The inspection apparatus of claim 1, wherein the outer stationary housing comprises a bottom surface configured to contact an area around the surface to be inspected.

9. The inspection apparatus of claim 1, wherein the outer stationary housing comprises three points of contact configured to contact an area around the surface to be inspected.

10. A inspection system comprising:
an inspection apparatus configured to adjustably hold an eddy current probe predetermined distance above a surface to be inspected, wherein the surface comprises an area surrounding a fastener, wherein the inspection apparatus comprises a rotation disk configured to spin the eddy current probe about an axis of rotation above the surface, wherein the inspection apparatus comprises an outer stationary housing within which the rotation disk is configured to spin; and
an alignment tool configured to adjust the predetermined distance of the eddy current probe above the surface and at a radial offset from the axis of rotation corresponding to a size of the fastener, wherein the alignment tool comprises an alignment pin against which the radial offset of the eddy current probe is configured to be set, and wherein the alignment tool comprises a probe height adjustment pad upon which the predetermined distance of the eddy current probe is configured to be set.

11. The inspection system of claim 10, wherein the inspection apparatus further comprises a slotted arm assembly that comprises a slotted arm with a first end pivotally mounted to the outer stationary housing and a second end slidably mounted to a probe bushing that securely holds the eddy current probe within the rotation disk, wherein the slotted arm assembly prevents the eddy current probe from rotating about a longitudinal axis of the eddy current probe when the eddy current probe rotates above the surface.

12. The inspection system of claim 10, wherein the inspection apparatus is configured for placement inside an outer rim of the alignment tool to adjust the radial offset of the eddy current probe.

13. The inspection system of claim 10, wherein the inspection apparatus is configured for placement on top of an outer rim of the alignment tool to adjust the predetermined distance of the eddy current probe.

14. The inspection apparatus of claim 8, wherein the bottom surface of the outer stationary housing is flat.

15. The inspection apparatus of claim 1, wherein the driving mechanism has frictional contact with the rotation disk.

16. The inspection apparatus of claim 15, wherein the driving mechanism comprises a rubber grommet forming the frictional contact with the rotation disk.

17. The inspection apparatus of claim 15, wherein the frictional contact allows for th driving mechanism to slip relative to the rotation disk.

18. The inspection system of claim 10, further comprising the eddy current probe, wherein the eddy current probe current radially abutted against the alignment pin of the alignment tool.

19. The inspection system of claim 10, further comprising the eddy current probe, wherein the eddy current probe longitudinally contacts the probe height adjustment pad of the alignment tool.

20. The inspection system of claim 12, wherein a bottom surface of the outer stationary housing contacts the outer rim of the alignment tool while adjusting the radial offset of the eddy current probe.

\* \* \* \* \*